United States Patent [19]

Penner et al.

[11] Patent Number: 5,725,519
[45] Date of Patent: Mar. 10, 1998

[54] STENT LOADING DEVICE FOR A BALLOON CATHETER

[75] Inventors: Abraham Penner, Tel-Aviv; Ofer Nativ, Rishon Lezion, both of Israel

[73] Assignee: Medtronic InStent Israel Ltd., Holon, Israel

[21] Appl. No.: 724,543

[22] Filed: Sep. 30, 1996

[51] Int. Cl.⁶ .................................................. A61B 19/00
[52] U.S. Cl. .................................................. 606/1; 606/198
[58] Field of Search ........................ 606/1, 108, 190.2; 29/234, 235, 282, 283

[56] References Cited

U.S. PATENT DOCUMENTS

| | | | |
|---|---|---|---|
| 5,437,083 | 8/1995 | Williams et al. | 606/1 |
| 5,626,604 | 5/1997 | Cottone | 606/108 |
| 5,628,754 | 5/1997 | Shevlin et al. | 606/108 |
| 5,630,830 | 5/1997 | Verbeek | 606/108 |

Primary Examiner—Glenn K. Dawson
Attorney, Agent, or Firm—Levisohn, Lerner, Berger & Langsam

[57] ABSTRACT

A device for loading a medical stent on a balloon catheter. A tube, preferable pre-installed with a stent, is secured to one component having a pulling knob. The tube with stent extends into the bore of a second component, also having a pulling knob. The bore of the second component is conical and reduces down in the direction of the first component. For intended use, the preselected balloon catheter is inserted within the confines of the lumen of the tube (which places it within the center of the stent). Then, the two knobs are pulled apart. The force of the pull causes the tube, with the stent around the catheter within it, to pass through the decreasing bore, thereby loading and compressing the stent onto the balloon catheter. The tube serves as the vehicle to carry the balloon catheter and stent through the bore for loading the stent onto the balloon catheter. The tube can be Teflon coated to facilitate the pulling and stent loading or, alternatively, the tube can be elastic and/or plastic.

21 Claims, 6 Drawing Sheets

STENT LOADING DEVICE FOR A BALLOON CATHETER

BACKGROUND OF THE INVENTION

The present invention relates to a device for loading a medical stent on a balloon catheter for use in a medical procedure. Stents are currently a very acceptable mechanism for treating a variety of medical conditions, but, in general, they are used at the site of a collapsed blood vessel to reopen the same and thereby permit normal blood flow. One current method of first locating and then releasing the stent at the site of need is by use of a balloon catheter which is threaded with the stent to the site. Then, the physician releases the stent from the catheter (by a mechanical release mechanism or by inflation of the balloon), inflates the balloon for stent deployment and the stent expands. The present invention relates to a device which enables the physician to load and secure the stent to the end of the balloon catheter with uniformity of application force, geometry, and ease. Use of the device allows the physician to locate the stent on the balloon catheter in an easily repeatable, structurally secure, tight and uniform manner. The device of the present invention results in the uniform crimping of the stent on the end of the balloon catheter. The device maintains the balloon's integrity, ensures that the stent is positively located at the desired position on the end of the balloon catheter and with the proper amount of holding force so that the stent will travel along with the catheter to the site of deployment and, yet, when and where so located, the stent can be easily released and inflated for its intended purpose. The device of the present invention reduces human errors and vagaries in the conventions human-hand crimping procedure.

According to the present invention, the loading of the stent onto the balloon catheter occurs by applying a uniform radially inward force on the stent which causes it to become crimped onto the distal end of the balloon catheter. The stent is loaded or secured to the catheter by use of a tube. The user pulls the catheter and stent, in the tube, through a conical orifice. In this manner the stent is uniformly, radially compressed around the catheter as it passes through the orifice. The cone-like or radial decreasing diameter of the orifice applies the radially compressive force to the stent, resulting in the stent becoming crimped onto the catheter.

DESCRIPTION OF THE PRIOR ART

The stent loading device of the present invention is related to the medical products field. Stents are currently used by physicians for the treatment of atherosclerotic stenones in blood vessels. In such a treatment procedure, a catheter is first introduced into the patient's blood vessel. Through this catheter, a guide wire is inserted for opening of the lesion. This is followed by a balloon catheter being inserted to the lesion region. The balloon end of the catheter is then inflated to increase the opening in the blood vessel's lumen. To maintain the opening in the lumen of the blood vessel, a stent is then inserted at the site. The stent is intended to keep the blood vessel open and to decrease the possibility of restenosis.

The stent is an intravascular prosthesis which is usually delivered to the lesion zone by attaching it to the tip of a balloon catheter. Prior to threading of the stent and balloon catheter through the blood vessel, followed by location of the balloon catheter and stent at the site, the stent is first "loaded" or secured to the end of the balloon catheter. The balloon catheter serves as the mechanism for locating the stent at the site of the lesion and, in addition, the balloon catheter serves as the mechanism for deployment, i.e., activation of the stent. More specifically, the stent is necessarily of reduced diameter while being threaded through the blood vessels of the patient until it reaches the site of deployment. After location is confirmed at the site of the lesion, the balloon catheter is inflated and the stent is released for residing at the site. Inflation of the balloon catheter causes the reduced diameter stent to revert or convert to a stent of relative increased diameter according to the balloon diameter and degree of inflation provided. The outside of the stent pushes against the inside wall of the otherwise collapsed blood vessel and, in this manner, the stent serves to maintain the lumen in a more open condition to allow for blood flow. The inflation of the balloon catheter causes the stent to expand to its open or enlarged condition/form, while pushing against the vessel wall and strengthening it. The balloon catheter is then deflated and removed from within the center of the stent, leaving the stent in place. The balloon catheter is then removed from the patient.

Today, there are several ways for loading or securing the stent on the end of the balloon catheter. The most common is by hand-crimping of the stent. The physician first selects the particular stent for use in the patient (taking into consideration diameter, length, and intended location). The physician also selects the desired and appropriate balloon catheter. Conventionally, the physician has manually crimped the stent to the end of the catheter and over the balloon tip by using his fingers. The result then is a crimped stent, surrounding the balloon end of the catheter. The manual manner of crimping, however, results in loaded stents, even with the same physician, which will vary in their uniformity, loading quality, and geometry, from loaded stent to stent. The holding force, reduced diameter, and uniformity of profile varies then, from stent crimp to stent crimp. Large variations exist, too, from one physician to another.

There is a need, therefore, for a mechanism which will facilitate the crimping and loading of a stent on a balloon catheter. The device should result in a stent loaded on the end of a balloon catheter which is uniform in its size, diameter, profile, strength of securement, etc. The present invention accomplishes these objectives.

In the current marketplace, i.e., before the present invention, there are several stent crimping devices. Basically, these are modified pliers. The instruments are not completely satisfactory in that there is still a wide divergence between application force, profile and stent diameter from stent application to another, even with the same physician doing the loading. Another device that was available before the present invention is a pre-crimped stent on a balloon catheter. This pre-loaded device has uniformity of securement of the stent to the balloon catheter but is problematic because of the large number of possible combinations between stents and balloon catheters. Each stent type, diameter, length, and anatomic location would have to be pre-loaded and available for each of the various balloon catheters. Obviously, this is a potentially large inventory for a physician to store.

Thus, standardized crimping of stents on balloon catheters exists and yet, the physician would be required to warehouse a wide variety of pre-crimped stents on catheters. Clearly, it is far preferable for the physician to be provided with a device which will allow the physician to select the balloon catheter appropriate for the patient, then, separately, select the stent for the patient, and then, using the present invention, allow the physician to uniformly and securely crimp that stent on the selected catheter.

SUMMARY OF THE PRESENT INVENTION

The present invention is a simple mechanical device which allows a physician to load, i.e., position and crimp a stent onto a balloon catheter. The proposed device is a mechanical implement which is manipulated by hand for loading the stent on the distal end of a balloon catheter. A first embodiment of the present invention contemplates the provision of a stent located or pre-installed within a plastic (such as Teflon) tube. Thus, consistent with the present invention, the stents are stored for future selection by the physician within the bore of a tube, the tube being held by one end of a separable pair of opposed gripping knobs. The physician will insert the desired balloon catheter into the open end of the device. The device can be provided with a wire which can be threaded down the longitudinal axis of the catheter to ensure that the lumen of the catheter is protected from collapsing during the procedure. With the balloon catheter located within the stent, with the stent located within the tube, the two knobs of the device are slowly pulled apart. This draws the tube (connected securely to the distal knob) through a reduced or conical bored section. As the knobs are pulled apart, the tube is uniformly reduced in diameter by it coming into contact with the reduced diameter side walls of the bore of the proximal component of the device. As this happens, the tube pulls the stent and balloon catheter along with it. This, in turn, causes the stent, contained within the tube to reduce in diameter and become secured to the balloon catheter. The thin guide wire passing down the longitudinal axis of the device, ensures that the lumen of the catheter does not collapse or become damaged during the process. Then, after the proximal end of the tube is fully passed through the reduced diameter bore of the proximal component of the device, the catheter, with the stent secured thereto, can be easily removed first from the tube and then threaded back through the distal end of the proximal component of the device. A uniformly loaded stent on a balloon catheter is the result. In one embodiment of the invention, the bore of the proximal component of the device is provided with a reverse or inverted conical bore portion, to facilitate the reverse passage of the balloon with loaded stent through the device.

To summarize, then, the present invention is the provision of a plastic hand-held device having, in the preferred embodiment, a stent pre-loaded within a tube. This eliminates the physician holding by hand the small and fragile stent. Actually, the stent is housed within a plastic or Teflon-coated tube (to ease passage through the bore) which itself is initially within the bore of a proximal component of the device. The other end of the tube is secured to the distal component. Both the proximal and the distal components of the device are provided with drawing knobs to facilitate pulling the components apart. Before pulling on the knobs, the selected catheter is threaded into the proximal component, such that its balloon end is within the center of the stent. The transparency of the device allows the physician to visually ensure proper location. Then, when so located, the knobs are pulled apart such that the distal component, securing one end of the tube (the other end extending into the bore of the proximal component and housing the stent, encircling the balloon tip of the catheter) is separated from the proximal component. Pulling the two components apart causes the tube, attached to the distal component, to pass through a cone-shaped bore of the proximal component. This reduces the diameter of the tube, which, in turn, by transfer of the compressive force, reduces the diameter of the stent, thereby collapsing and securing it around the balloon catheter. In this manner, the device operates in a fashion similar to metal rod swaging through a die. Since there is no relative movement between the stent, the balloon catheter and the plastic tube, the stent and balloon are pulled through the reducing bore of the proximal component. The reducing bore of the proximal component causes a uniform radially inward force to compress the stent onto the balloon tip. In this manner, the stent is crimped onto the balloon.

After the two components are fully separated, the balloon catheter, with stent secured to its tip, is first removed from the tube. Then, the balloon catheter and stent are removed from the proximal component. This is accomplished, according to the preferred embodiment, by reverse passing of the tip of the balloon catheter through the proximal component. This movement is facilitated by the provision of an inverted cone shaped bore-portion of the reducing bore of the proximal component. This facilitates the removal of the balloon catheter and stent from the bore of the device.

The mechanism and procedure results in a uniform, repeatable and tight loading of the stent that substantially preserves the stent's original configuration, albeit in a reduced diameter. By utilization of the stent loading device, the physician can select the appropriate balloon catheter for the specific patient and treatment, without the need to manually hold a large inventory of possible pre-loaded combinations of stents and balloon catheters. As mentioned, in the preferred embodiment, the stent is pre-installed in the stent loading device, within the plastic tube. This eliminates the need to hold the small and fragile stent.

DETAILED DESCRIPTION OF THE FIGURES AND THE PREFERRED EMBODIMENT

Figure 1:
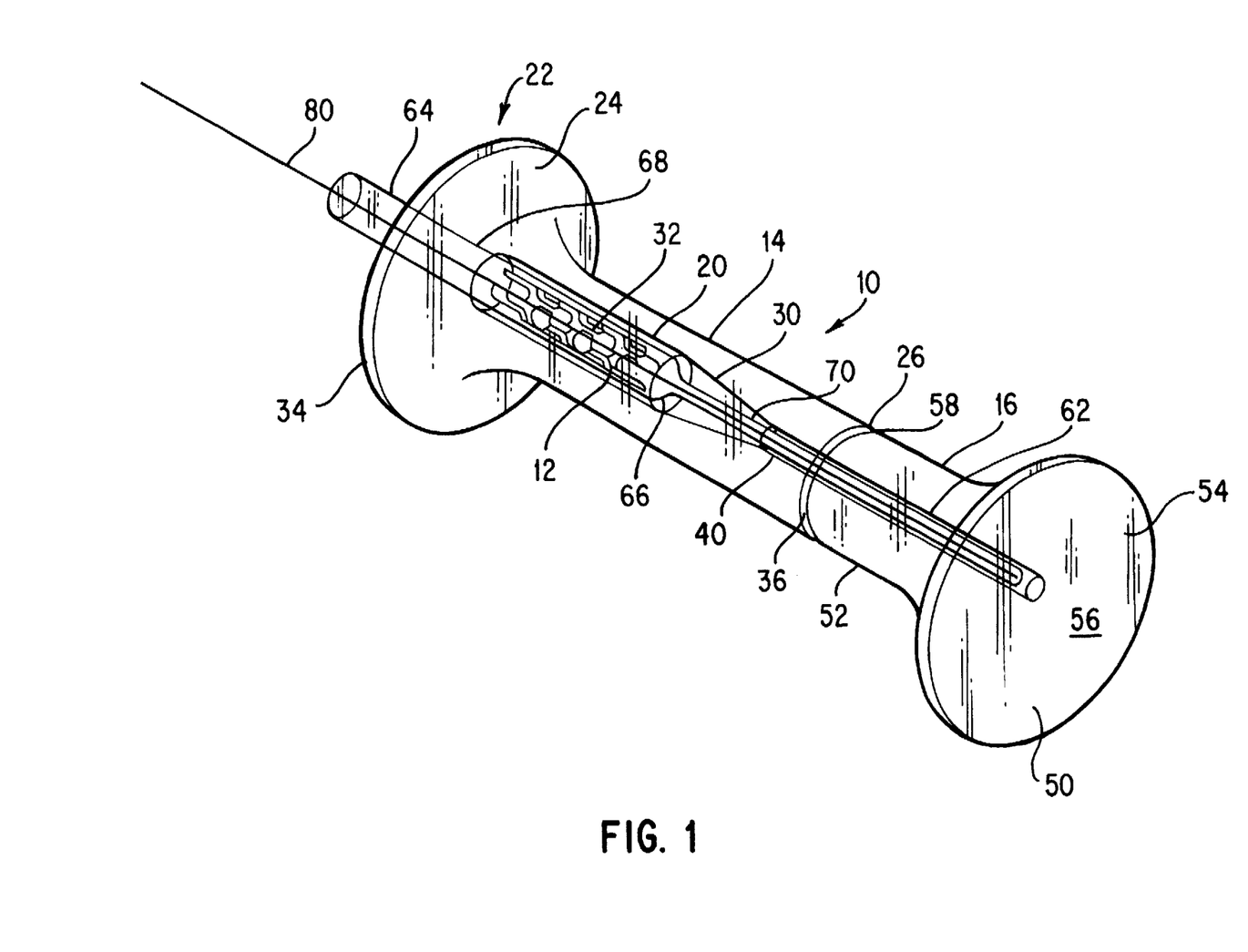
FIG. 1 is a perspective view of the preferred embodiment of the invention, showing the stent loading device before it has been used. In this embodiment, the stent is pre-installed within a Teflon-coated or other plastic-like tube. A metal wire is provided, passing through the longitudinal center of the tube and the stent. This FIGURE shows the device before the insertion of a balloon catheter, upon which the stent is intended to be loaded.

The stent loading device 10 is shown in FIG. 1. It represents the preferred embodiment of the present invention. In this configuration, the stent 12 is supplied as a pre-installed component. Providing the stent 12 as a pre-installed component eliminates the need for the physician to manually touch the stent during the loading procedure. This is desirable since the stent is small and fragile. Pre-installing the stent 12 reduces the possibility of dropping or inappropriately handling the stent before the medical insertion procedure. The device 10 is preferably made from a clear, rigid plastic so that the physician can see the location of the pre-installed stent 12, prior to the insertion of the balloon catheter, and during the stent loading procedure. The device 10 comprises a proximal component 14 and a distal component 16. Proximal component 14 has a reducing-diameter bore or orifice 20 passing through and along the longitudinal axis of the proximal component. The orifice 20 extends from the proximal end 22 of the knob 24 to the distal end 26 of the proximal component 14. The orifice, in the preferred embodiment, comprises a uniform, relatively large diameter section, commencing at the proximal end 22 of the knob 24, and necks down into a conical portion 30 which terminates at the distal end 26 of the proximal component. The diameter of the orifice at the proximal end, adjacent the knob 24, is sufficiently large such that a balloon catheter BC can be easily inserted and threaded therein. The diameter of the orifice 20 at the distal end 26 of the proximal component 14 is significantly smaller than the diameter of the orifice 20 at the proximal end 22, and yet allows the tube and central wire (described hereinafter), the balloon catheter BC and the stent 12 to pass therethrough, albeit with a manual pulling force since the inside wall of the conical portion 30 swages i.e., reduces in diameter, the stent 12, onto the tip of the balloon catheter BC. The diameter of the stent 12 is reduced and secured to the tip of the balloon catheter BC as the tube, wire, stent 12 and balloon catheter BC are pulled through the orifice 20. The transfer of the pulling force into a radial compressive force is facilitated by the relative low frictional resistance provided by the tube 64.

In the preferred embodiment of the present invention, the proximal component 14 is molded from a single piece of clear, rigid plastic and the knob 24 has a smooth curved outer wall which gently merges into the cylindrical outer wall 32. A flat, circular end 34 is provided at the proximal end 22 of the proximal component 14, defining one end of the knob 24, and a flat, circular end 36, of smaller relative diameter to that of flat end 34, is located at the distal end 26 of the proximal component 14. In the preferred embodiment of the present invention, the orifice 20 also includes a downstream, reduced and uniform diameter section 40, extending between the conical portion 30 and the flat end 36.

In the preferred embodiment of the present invention, a portion of the downstream, reduced and uniform diameter section 40, adjacent to the flat end 36, is an inverted conical section 42 (see FIG. 3), with its wider mouth being located at the flat end 36 and its smaller opening upstream, i.e., more proximally located. This, as will be more fully explained hereinafter, facilitates the easy and uneventful removal of the proximal component from the balloon catheter with loaded stent.

The distal component 16 is also made from rigid, transparent plastic and comprises a knob 50 extending and gradually merging into a cylindrical portion 52. One end 54 (the distal end) of the distal component 16 constitutes a flat, circular disk 56, which defines the end of the knob 50. The other or proximal end 58 of the distal component 16, i.e., the end which opposes and mates with the distal end 26 or the flat end 36 of the proximal component 14, is also a flat disk 60 of relative reduced diameter in comparison to the diameter of the disk 56. The diameter of disk 56 of the distal component 16 is about the same as that of the flat, circular end 34 of proximal component 14. Similarly, the flat end 36 of proximal component 14 is about the same size as the flat end 58 of distal component 16. Extending between disk 56, at the distal end 54 of the distal component 16 and the disk 60 of proximal end 58 of the distal component is a constant diameter bore 62. A Teflon coated or plastic tube 64 is secured within bore 62 and extends beyond the proximal end 58 of the distal component. The tube 64 extends into the orifice 20 of the proximal component 14, at least before pulling the components apart for stent loading. According to the preferred embodiment of the invention, the tube 64 extends beyond flat end 34 of the proximal component 14 (see FIG. 1). The Teflon-coated tube is squeezable, i.e., it will reduce in diameter as it passes through the small diameter of conical portion 30. In its original shape, tube 64 is of a constant diameter throughout the bore 62 of the distal component 16. Originally, i.e., before the two knobs are pulled apart, the end of the tube 64 which extends into the orifice 20 is of a larger diameter. In the preferred embodiment of the present invention, the tube 64 extends upstream and beyond the knob 24 of the proximal component (see FIG. 1 ), at least it extends there when the proximal end 58 of the distal component is closely adjacent and flush with the distal end 26 of the proximal component 14. In the preferred embodiment of the invention, the tube 64 is of a larger relative diameter for that portion originally located within the orifice yet upstream, i.e., proximally, of the conical portion 30 of the orifice 20. A smooth walled neck portion 66 connects the enlarged diameter portion 68 of the tube 64 (within the orifice 20) to the reduced diameter portion 70 of tube 64, located at or about the upstream end of the conical portion 30 of orifice 20. The outside diameter of the reduced diameter portion 70 is about that of the inside diameter of the bore 62 so that a snug fit is achieved. Pulling on the distal component 16, pulls the tube 64 along with it. In one embodiment, a commercial adhesive or bonding can be used to ensure a tight fit between the tube 64 and the distal component 16 so that they move in tandem.

A wire 80 is also secured to the distal component 16, axially located within the bore 62 and the tube 64. The wire 80 is of relative small diameter and extends from the distal component, through the distal end 26 of the proximal component, through the reduced diameter section 40 of the orifice 20, through and beyond the proximal end 22 of the proximal component 14. FIG. 1 shows the wire 80 in its original position, i.e., extending out of the tube 64, beyond the knob 24 of the proximal component. The wire 80 extends beyond the end of the tube 64. The fixed end of the wire is secured to the distal component 16 so that the distal component, the wire and the tube all move in unison.

The diameter of the orifice 20 of the device 10, at the distal end 26, is preferably the diameter desired for the stent to be crimped and secured to the balloon catheter. The diameter is about 0.3 mm less than the sum of the original (pre-loaded) outer diameter of the stent 12 and the wall thickness of the Teflon tube 64. The decrease in the orifice's inner diameter, to the dimension at the location of the distal end 26, is at least initially gradual, to minimize the force needed for smooth and easy crimping. The Teflon tube 64 is preferably 1.7 mm inside diameter, having about a 2.1 mm outside diameter. The metal wire 80 is preferably stainless steel and is about 0.3 3 mm in diameter. The wire 80 extends down the center line of the tube 64, through the orifice 20. As mentioned, it, too, is secured to the distal component 16. The purpose of the wire 80 is to protect the lumen of the balloon catheter, as the stent is crimped onto the tip of the same. More specifically, the wire provides a support surface to the interior of the balloon catheter during the crimping of the stent to the balloon catheter.

Figure 2:
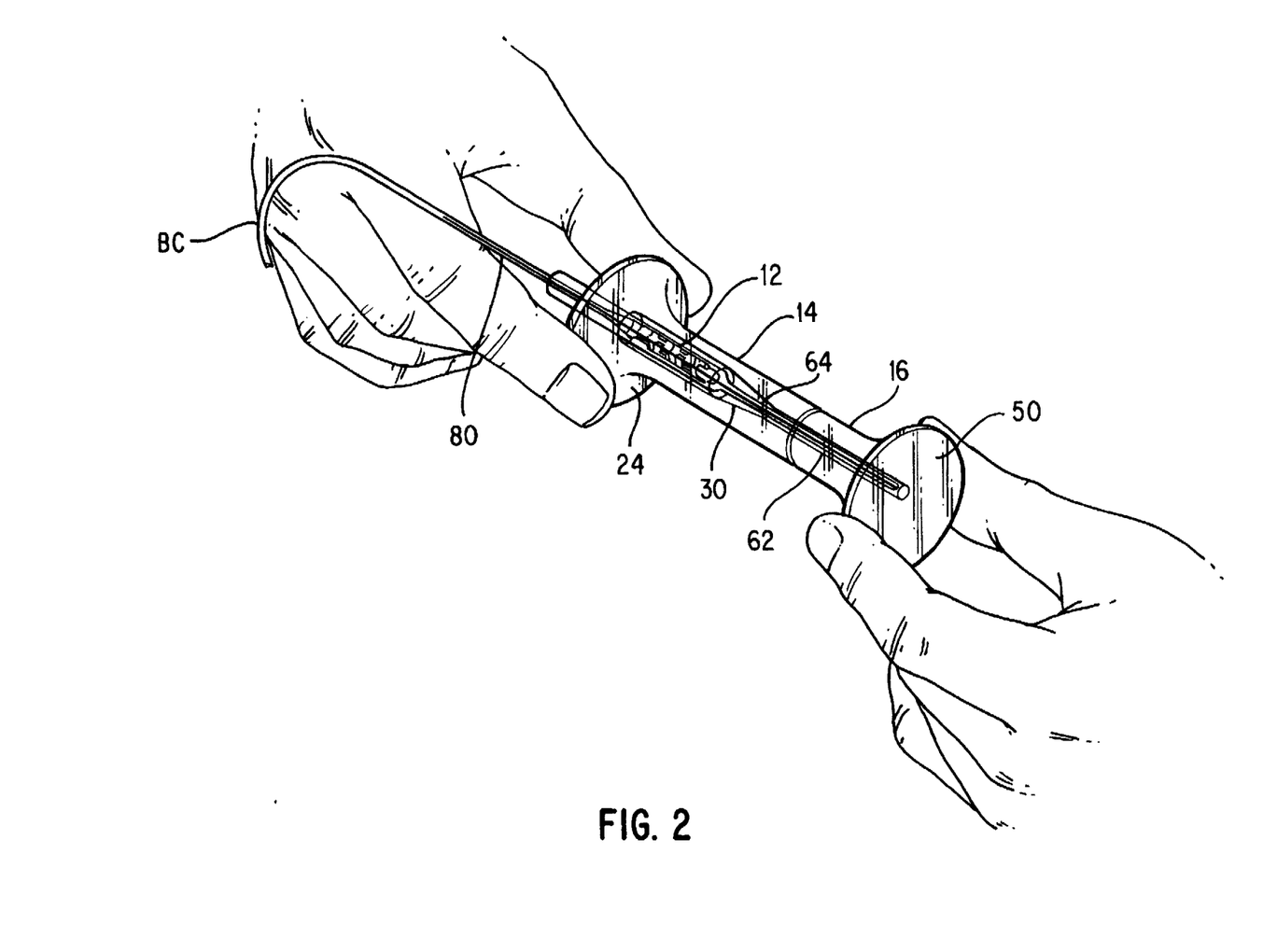
FIG. 2 is another perspective view of the present invention, after the balloon catheter has been inserted such that its balloon tip is located within the stent (pre-installed in the plastic tube). The device is shown just before the two components, the proximal and the distal components, are to be pulled apart for stent loading. The physician's hands are visible as they would be in contact with the knobs of the two components. The metal wire is shown threaded down the axis of the balloon catheter and protects against the collapse of the lumen of the balloon catheter during stent loading.

In operation, a device 10 with the correct size and type stent is selected from the physician's inventory. Then the appropriate balloon catheter BC is selected. The physician then inserts the wire 80 into the lumen of the balloon catheter as the tip of the balloon catheter is slid or threaded into the tube 64. The balloon catheter is pushed into the tube 64 until the physician sees that the tip of the balloon catheter is slightly beyond the distal end of the pre-installed stent 12. Since the device is visually transparent, the physician can easily locate the balloon at the desired location relative to the stent. This is depicted in FIG. 2.

Figure 3:
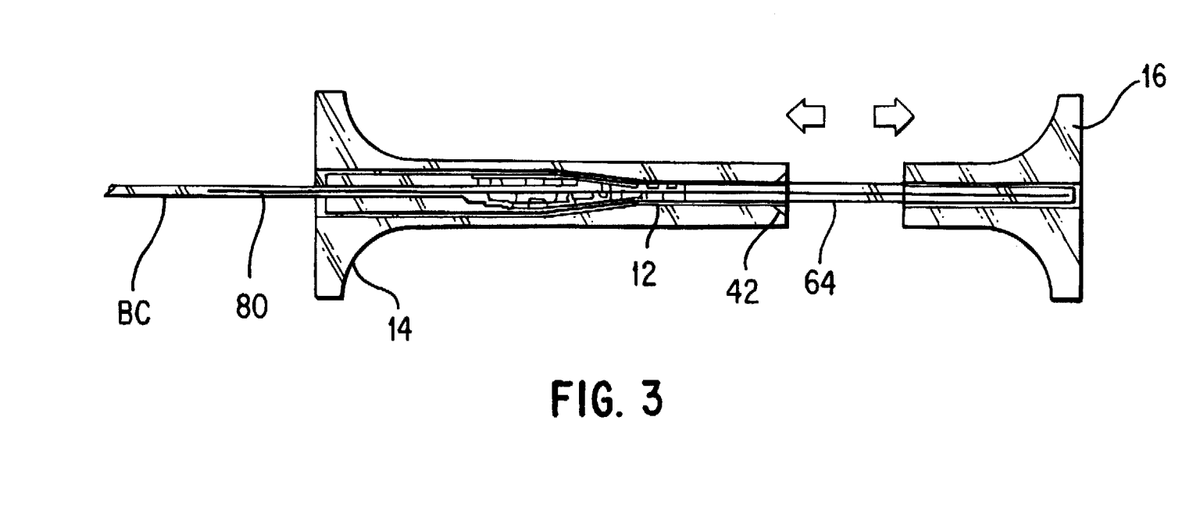
FIG. 3 is a reduced, cross-sectional view of the device, shown at the middle of the stent loading or mid-crimping stage.
Figure 4:
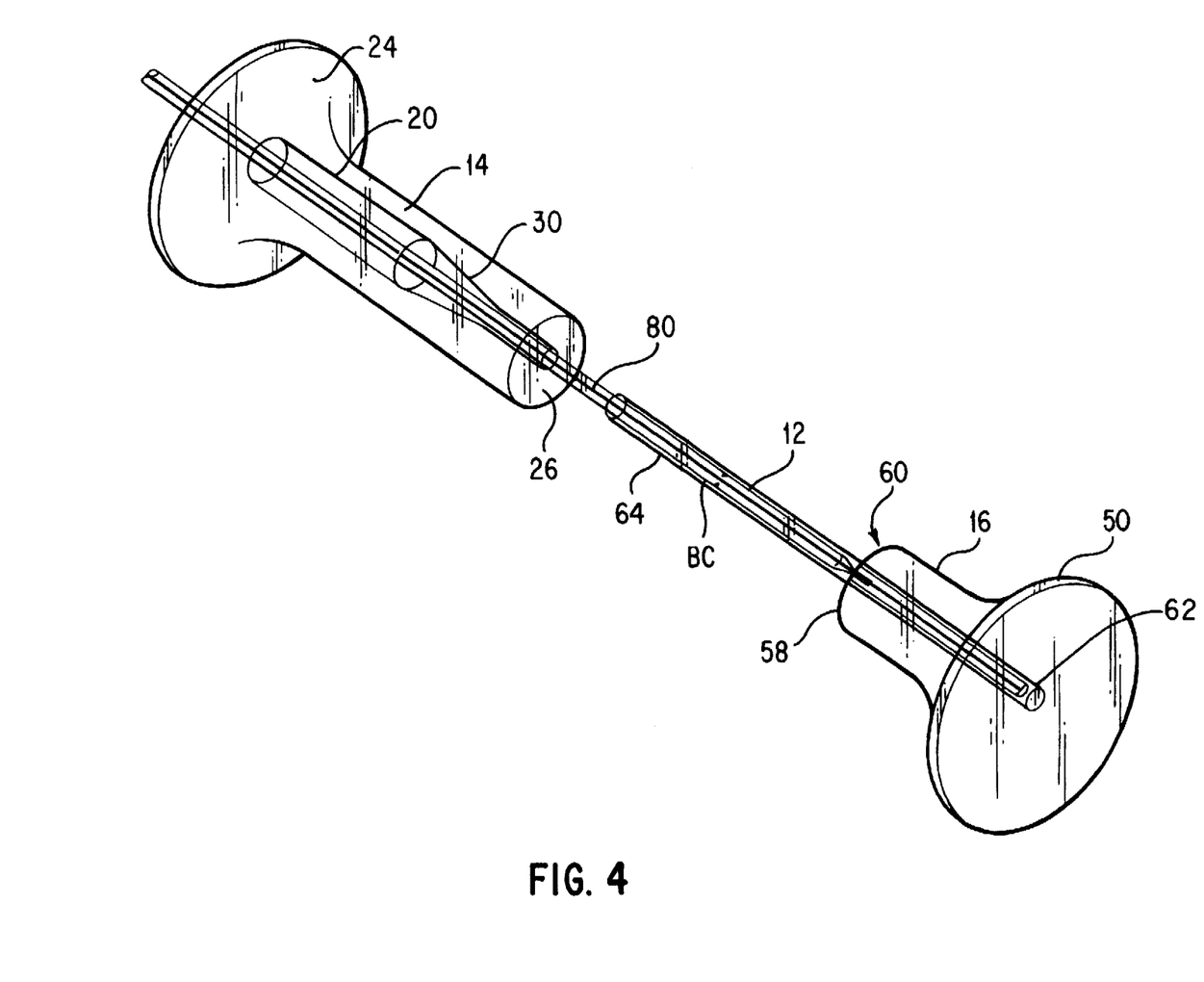
FIG. 4 is another perspective view of the device, after the proximal and distal components have been pulled apart. This FIGURE shows the relative location of the plastic coated or Teflon tube after the proximal and distal components have been separated. The metal wire, extending through the reducing-diameter bore or orifice of the proximal component is also shown. The stent and balloon catheter have been pulled through the bore of the proximal component by the gripping action of the Teflon or plastic tube as it passes through the bore.
Figure 5:
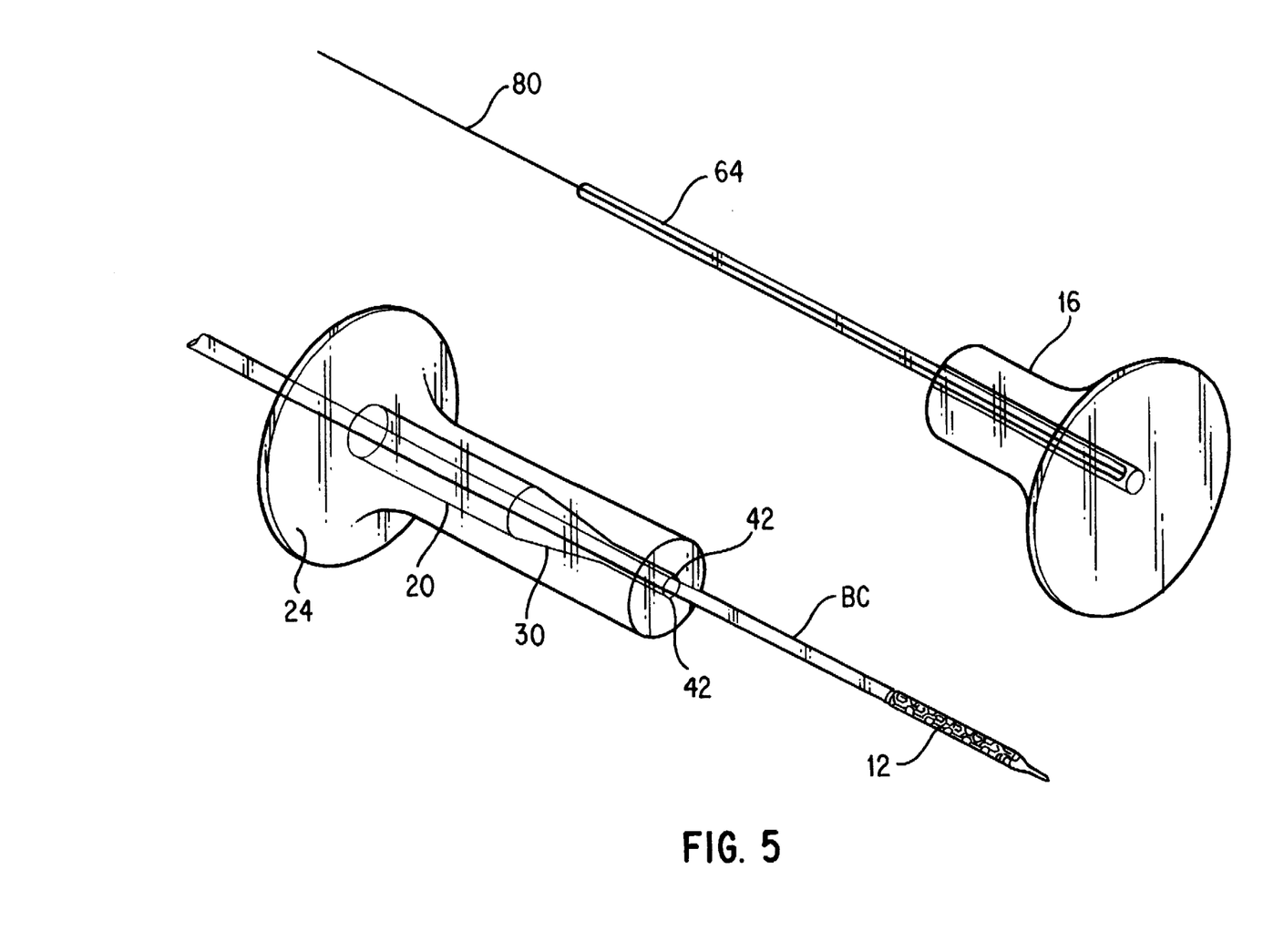
FIG. 5 is a perspective, exploded view of both the proximal (bottom-most) and distal (top-most) components, after the stent and balloon catheter have passed through the diameter-reducing bore or orifice of the proximal component. As can be seen, the stent is now crimped or loaded onto the balloon tip of the catheter. The distal component with the attached tube and the metal wire have been removed from the balloon catheter and stent, thereby exposing the stent and the balloon tip. The FIGURE shows the loaded stent on the balloon catheter after the Teflon tube and the metal wire have been pulled through the bore.
Figure 6:
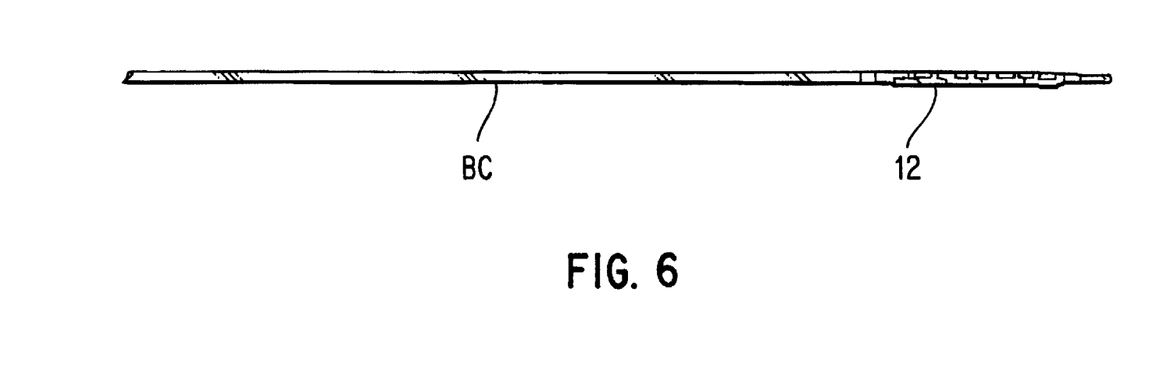
FIG. 6 is a side elevational view of the crimped stent on the balloon catheter, after it has been pulled backwardly through the reducing-diameter bore or orifice, thereby removing the proximal component of the crimping or loading device from the stent-loaded catheter.

The next step is for the physician to start pulling the knob 24 away and apart from knob 50, thereby separating proximal component 14 from that of distal component 16. This is shown in FIG. 3. Pulling the knobs apart causes the Teflon tube 64, connected to distal component 16, to travel along the longitudinal axis of the device, i.e., down the orifice 20 of the proximal component. The balloon catheter BC and the stent 12, within the tube 64, similar move through the orifice 20, within the tube 64, since there is no relative movement between the elements. The tube 64 grips and carries the balloon catheter and stent along with it, through the conical portion 30 of orifice 20. The gradual decrease in the diameter of the orifice 20, along conical portion 30, applies a radial compressive force on the Teflon tube 64. The Teflon tube 64, in turn, transfers this compressive force onto the stent. The radial compressive force is uniform and causes the stent to reduce in diameter as it passes through the conical portion 32 of the orifice 20. This results in the stent becoming crimped onto the balloon catheter. This results in the desired loading of the stent 12 onto the balloon catheter BC. Continuing the pulling apart of the knobs ultimately results in the tube 64 clearing out of the distal end 26 of the proximal component. This results, of course, in the clearance, too, of the stent 12 and the tip of the balloon catheter BC beyond the distal end 26. This is shown in FIG. 4. Here, it can be seen, that the stent is loaded onto the tip of the balloon catheter. Next, the Teflon tube 64 and the metal wire 80 are pulled off of the stent and from the balloon catheter. This is done by holding the catheter and pulling the distal component 16 with its tube 64 off of the stent-loaded catheter. The result is shown in FIG. 5. The proximal component 14 must then be removed, too. This is accomplished by pulling the balloon catheter, loaded with the now-compressed stent 12, back through the orifice 20 of the proximal component. Since the Teflon tube 64 has already been removed, this step is relatively effortless. An inverted conical section 42 (see FIG. 3), at the distal end 26 of the proximal component 14, facilitates the threading of the stent and tip of the balloon catheter, as the same is removed from the proximal component. The inverted conical section 42 minimizes the impedance provided to the balloon-stent, as they pass back through the orifice 20. The end product is a crimped stent on the tip of the balloon catheter BC. This is shown in FIG. 6.

Another embodiment of the present invention comprises the use of an interchangeable or variable orifice so that the same loading device 10 may be used for several different profile/size/shaped balloons. The orifice diameter can be changed in many ways. A typical example for performing this function would be to use a hole in a cone made of a semi-rigid material (such as Teflon or PEEK) as the orifice. Then, by pressing the cone against the conic hole with angles different from those of the cone, the hole in the cone tends to reduce its diameter. The final orifice diameter depends on the force applied on the cone.

Yet another embodiment of the present invention includes the use of an orifice made from a flexible material, such as Nylon. When a low profile balloon catheter is used, the force applied by the orifice and on it is relatively small. However, when a high profile balloon catheter is to be used, the crimping force is necessarily larger, which causes the orifice to increase its diameter. The result is that such an orifice applies an almost constant force onto the stent. Such a loading device is suitable for a wide variety of balloon catheter profiles.

Another embodiment of the present invention contemplates the use of a constant orifice. However, instead of using a Teflon-coated tube, a more flexible tube such as Nylon or silicon is used. When pulling the tube, stent and balloon catheter, through the orifice, the tube elongates according to the profile of the orifice and the impedance provided by the orifice. When using a low profile balloon, the impedance is small and the tube wall thickness remains almost unchanged. When a high profile or diameter balloon catheter is to be used, a high impedance on the passage of the tube through the orifice results. Thus, the tube elongates and the wall thickness decreases. The force applied by the orifice on the tube decreases, resulting in a relative constant compressive force to the stent, similar to the just described embodiment.

Figures 7, 7A, 7B:
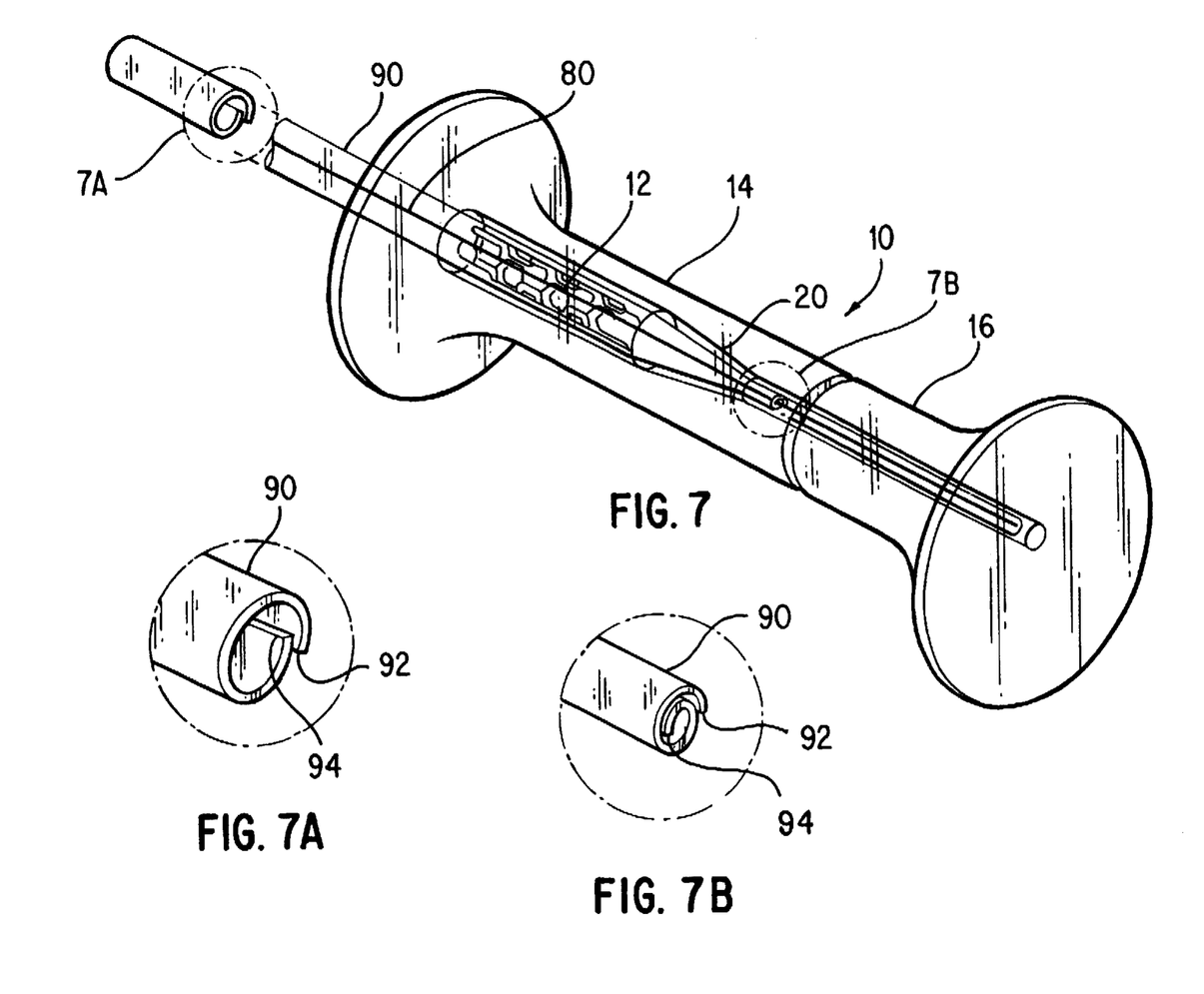
FIG. 7 is a perspective view, similar to FIG. 1, showing an alternate embodiment of the plastic/Teflon tube.

FIG. 7 shows an alternate embodiment of the present invention. The device 10 still comprises a proximal component with an orifice and a distal component holding a tube. However, in this embodiment, the tube is sliced along its longitudinal axis. Thus, as the tube passes through the orifice, the diameter of the tube decreases since the cut edge of the tube slides along the other edge of the tube. The inset drawings in FIG. 7 show the cross section of the tube 90 with its edges 92 and 94. The first inset A of FIG. 7 shows the tube and its relative diameter before the knobs of the device have been pulled apart, while the second inset B of FIG. 7 shows the tube 90 and its smaller relative diameter at the location of the tube within the decreased or reduced, constant diameter section 40 of the orifice 20. The longitudinal slit of the tube 90 facilitates the drawing down of the diameter of the tube and the stent to the diameter required to secure it to the tip of the balloon catheter.

Another alternate embodiment of the present invention is the provision of a tube made of mesh. This type of tube has the functional ability to "shrink" on the stent as the crimping procedure progresses and the stent diameter decreases. The advantage of the mesh over a solid tube resides in its ability to sustain very large deformations, much higher than that of a tube made of solid, non-flexible and difficult to crush material. The mesh material of the tube will still grab the stent and balloon catheter to pull them through the conical portion 30 and, yet, the mesh is far easier to collapse or reduce in diameter than a solid tube.

Although particular embodiments of the present invention have been shown and described, modification may be made to the device without departing from the teachings of the present invention. Accordingly, the present invention comprises all embodiments within the scope of the appended claims.

We claim as follows:

1. A device for loading a stent onto a balloon catheter comprising:
   (a) a proximal component having an orifice with a gradually tapering portion sized and configured to be smaller in diameter than the diameter of said stent prior to loading and passing therethrough, and a first pulling means for facilitating movement of said proximal component;
   (b) a distal component having a tube secured thereto and extending therefrom and into said orifice, said tube having an original diameter sized to hold a tip of a balloon catheter within a stent, and second pulling means for facilitating relative movement of said distal component with respect to said proximal component, such that movement of said proximal component with respect to said distal component causes said tube, the stent and the tip of a balloon catheter to pass through said gradually tapering portion of said orifice thereby crimping the stent onto the tip of said balloon catheter.

2. A device for loading a stent onto a balloon catheter as claimed in claim 1 wherein said gradually tapering portion comprises a conical section of gradual reduced diameter.

3. A device for loading a stent onto a balloon catheter as claimed in claim 1 wherein said tube is formed from a material which minimizes the frictional resistance of the passage of said tube through said orifice.

4. A device for loading a stent onto a balloon catheter as claimed in claim 3 wherein said tube is made from Teflon.

5. A device for loading a stent onto a balloon catheter as claimed in claim 1 wherein said tube is elastically deformable.

6. A device for loading a stent onto a balloon catheter as claimed in claim 1 wherein said distal component is provided with a wire for protecting the lumen of said balloooon catheter, said wire extending through said tube and said orifice of said proximal component prior to use of the device.

7. A device for loading a stent onto a balloon catheter as claimed in claim 1 wherein said proximal component and tube are transparent.

8. A device for loading a stent onto a balloon catheter as claimed in claim 1 wherein said orifice is further provided with a constant diameter section, distal to said gradual, reducing diameter portion.

9. A device for loading a stent onto a balloon catheter as claimed in claim 1 wherein said proximal component has a proximal end and a distal end and said distal component comprises a proximal end and a distal end, said distal end of said proximal component mating with said proximal end of said distal component.

10. A device for loading a stent onto a balloon catheter as claimed in claim 1 wherein a section of said orifice is provided with an inverted conical portion.

11. A device for loading a stent onto a balloon catheter as claimed in claim 1 wherein said orifice has a reducing diameter portion and the smallest diameter of said reducing diameter portion is slightly less than the sum of the outer diameter of the stent before loading and the thickness of said tube.

12. A device for loading a stent onto a balloon catheter as claimed in claim 1 wherein said smallest diameter of said reducting diameter portion is about 0.3 mm less than the sum of the outer diameter of the stent before loading and the thickness of said tube.

13. A device for loading a stent onto a balloon catheter as claimed in claim 1 in combination with a stent is preinstalled within said tube.

14. A device for loading a stent onto a balloon catheter as claimed in claim 1 wherein said tube comprises a longitudinal slit to facilitates its compression as it passes through said orifice during pulling apart of said proximal component from said distal component.

15. A device for loading a stent onto a balloon catheter as claimed in claim 1 wherein said orifice causes uniform radial compression and loading of a stent onto the tip of a balloon catheter as a consequence of said proximal component being pulled away from said distal component, causing said tube, a stent and a tip of a balloon catheter pass through said orifice.

16. A device for loading a stent onto a balloon catheter as claimed in claim 1 wherein said first and second pulling means are finger gripping knobs.

17. A device for loading a stent onto a balloon catheter as claimed in claim 1 wherein said tube is made from mesh-like material.

18. A method of loading a stent onto a balloon catheter comprising the steps of:
   (a) providing a proximal component with an orifice passing therethrough,
   (b) providing a distal component with a tube secured thereto, said tube extending therefrom and having a first end extending into said orifice;
   (c) placing a stent within said first end of said tube;
   (d) placing a balloon catheter within said stent; and
   (e) moving said proximal component with respect to said distal component such that said tube, stent and said balloon catheter are pulled through said orifice crimping said stent to said balloon catheter.

19. A method of loading a stent onto a balloon catheter as claimed in claim 18 wherein said orifice has a gradual reducing diameter portion.

20. A method of loading a stent onto a balloon catheter as claimed in claim 19 wherein said orifice radially compresses said stent onto said balloon catheter.

21. A method of loading a stent onto a balloon catheter as claimed in claim 19 further comprising the step of removing said tube from said stent-loaded balloon catheter after said step (e) is performed.

* * * * *